US009119926B2

(12) United States Patent
Cuevas et al.

(10) Patent No.: US 9,119,926 B2
(45) Date of Patent: Sep. 1, 2015

(54) SUBGLOTTIC SUCTIONING SYSTEM

(75) Inventors: Brian J. Cuevas, Cumming, GA (US);
Joseph A. Cesa, Cumming, GA (US);
Scott M. Teixeira, Cumming, GA (US);
Michael Sleva, Atlanta, GA (US);
Adrienne A. Hershey, Cumming, GA (US); Stephen A. Baratian, Roswell, GA (US)

(73) Assignee: AVENT, INC., Alpharetta, GA (US)

( * ) Notice: Subject to any disclaimer, the term of this patent is extended or adjusted under 35 U.S.C. 154(b) by 889 days.

(21) Appl. No.: 12/533,531

(22) Filed: Jul. 31, 2009

(65) Prior Publication Data

US 2011/0023884 A1 Feb. 3, 2011

(51) Int. Cl.
*A61M 16/04* (2006.01)
*A61M 1/00* (2006.01)
*A62B 9/02* (2006.01)
*A62B 9/06* (2006.01)

(52) U.S. Cl.
CPC ............. *A61M 16/04* (2013.01); *A61M 1/0062* (2013.01); *A61M 1/0084* (2013.01); *A61M 16/0463* (2013.01); *A61M 16/0465* (2013.01); *A61M 16/0479* (2013.01); *A61M 16/0486* (2013.01); *A61M 1/0064* (2013.01); *A61M 16/0434* (2013.01)

(58) Field of Classification Search
USPC ........ 128/207.14–207.16; 604/119, 183, 163, 604/171, 250, 251, 118, 172, 263, 266, 267, 604/35, 36, 43, 45, 514, 540, 902; 251/214, 251/337, 321, 330; 137/381
See application file for complete search history.

(56) References Cited

U.S. PATENT DOCUMENTS

| 4,240,417 | A | | 12/1980 | Holever |
| 4,305,392 | A | | 12/1981 | Chester |
| 4,584,998 | A | | 4/1986 | McGrail |
| 4,680,026 | A | * | 7/1987 | Weightman et al. ............ 604/33 |
| 4,696,669 | A | | 9/1987 | Menhusen |
| 5,083,561 | A | | 1/1992 | Russo |

(Continued)

FOREIGN PATENT DOCUMENTS

| CN | 201048980 Y | 4/2008 |
| JP | 2003-093511 A | 4/2003 |

(Continued)

*Primary Examiner* — Tan-Uyen (Jackie) T Ho
*Assistant Examiner* — Mark Wardas
(74) *Attorney, Agent, or Firm* — Dority & Manning, PA

(57) ABSTRACT

A subglottic suctioning system with a tracheal tube having a ventilation lumen, a cuff inflation lumen, and a suction lumen are disclosed which may help reduce the incidence of ventilator associated (or acquired) pneumonia. The suction lumen communicates with the space in the trachea above the cuff where secretions accumulate. The suction lumen has a valve on the proximal end for connection to a source of vacuum. The valve is adapted to interrupt the supply of vacuum to the suction lumen to allow for the introduction of a rinsing fluid in its place and to automatically re-establish the connection to the source of vacuum upon completion of rinsing. The rinsing fluid aids in maintaining an open suction lumen and may include medicaments and mucolytic agents to enhance or promote healing or to alter the properties of the mucus to make removal easier. The user may easily and repeatedly alternate suction and rinsing fluid through the suction lumen, i.e., the user may "pulse" the line to loosen, break up and remove secretions and deposits that may partially or completely block or clog the suction lumen.

4 Claims, 17 Drawing Sheets

(56) References Cited

U.S. PATENT DOCUMENTS

| | | | |
|---|---|---|---|
| 5,139,018 A | 8/1992 | Brodsky et al. | |
| 5,146,916 A | 9/1992 | Catalani | |
| 5,174,283 A | 12/1992 | Parker | |
| 5,193,544 A | 3/1993 | Jaffe | |
| 5,201,310 A | 4/1993 | Turnbull | |
| 5,207,641 A | 5/1993 | Allton | |
| 5,279,549 A * | 1/1994 | Ranford | 604/34 |
| 5,285,778 A | 2/1994 | Mackin | |
| 5,290,263 A * | 3/1994 | Wigness et al. | 604/247 |
| 5,354,267 A * | 10/1994 | Niermann et al. | 604/32 |
| 5,513,627 A | 5/1996 | Flam | |
| RE35,531 E | 6/1997 | Callaghan et al. | |
| 5,735,271 A | 4/1998 | Lorenzen et al. | |
| 5,738,648 A | 4/1998 | Lands et al. | |
| 5,832,920 A | 11/1998 | Field | |
| 5,845,634 A | 12/1998 | Parker | |
| 5,976,072 A | 11/1999 | Greenberg | |
| 6,116,243 A | 9/2000 | Pagan | |
| 6,119,695 A | 9/2000 | Augustine et al. | |
| 6,152,136 A | 11/2000 | Pagan | |
| 6,261,401 B1 | 7/2001 | Pagan | |
| 6,427,686 B2 | 8/2002 | Augustine et al. | |
| 6,546,931 B2 | 4/2003 | Lin | |
| 6,668,821 B2 | 12/2003 | Christopher | |
| 6,668,832 B2 | 12/2003 | Hipolito et al. | |
| 6,705,321 B2 | 3/2004 | Cook | |
| 6,978,783 B2 | 12/2005 | Svendsen | |
| 7,004,169 B2 | 2/2006 | Brain | |
| 7,025,755 B2 * | 4/2006 | Epstein | 604/500 |
| 7,040,322 B2 | 5/2006 | Fortuna | |
| 7,469,700 B2 * | 12/2008 | Baran | 128/207.14 |
| 2001/0001059 A1 * | 5/2001 | Love | 435/7.1 |
| 2001/0023312 A1 | 9/2001 | Pacey | |
| 2001/0044600 A1 | 11/2001 | Elkins | |
| 2004/0007236 A1 | 1/2004 | McGee | |
| 2005/0197645 A1 | 9/2005 | Karpowicz et al. | |
| 2005/0284482 A1 * | 12/2005 | Patel | 128/207.14 |
| 2005/0284483 A1 * | 12/2005 | Patel | 128/207.14 |
| 2006/0162730 A1 | 7/2006 | Glassenberg et al. | |
| 2007/0044807 A1 * | 3/2007 | Madsen et al. | 128/207.15 |
| 2007/0089748 A1 * | 4/2007 | Madsen et al. | 128/207.15 |
| 2007/0199460 A1 | 8/2007 | Cyman et al. | |
| 2008/0053454 A1 | 3/2008 | Pasillas et al. | |
| 2008/0121236 A1 * | 5/2008 | Field | 128/207.15 |
| 2009/0038620 A1 * | 2/2009 | Efrati | 128/207.14 |
| 2009/0071484 A1 | 3/2009 | Black et al. | |
| 2009/0090366 A1 | 4/2009 | Cuevas et al. | |
| 2010/0249732 A1 * | 9/2010 | Fleischmann | 604/305 |

FOREIGN PATENT DOCUMENTS

| | | |
|---|---|---|
| JP | 2004-283329 A | 10/2004 |
| WO | WO 99/38548 A2 | 8/1999 |
| WO | WO 2007/024288 A1 | 3/2007 |
| WO | WO 2008/023147 A1 | 2/2008 |

* cited by examiner

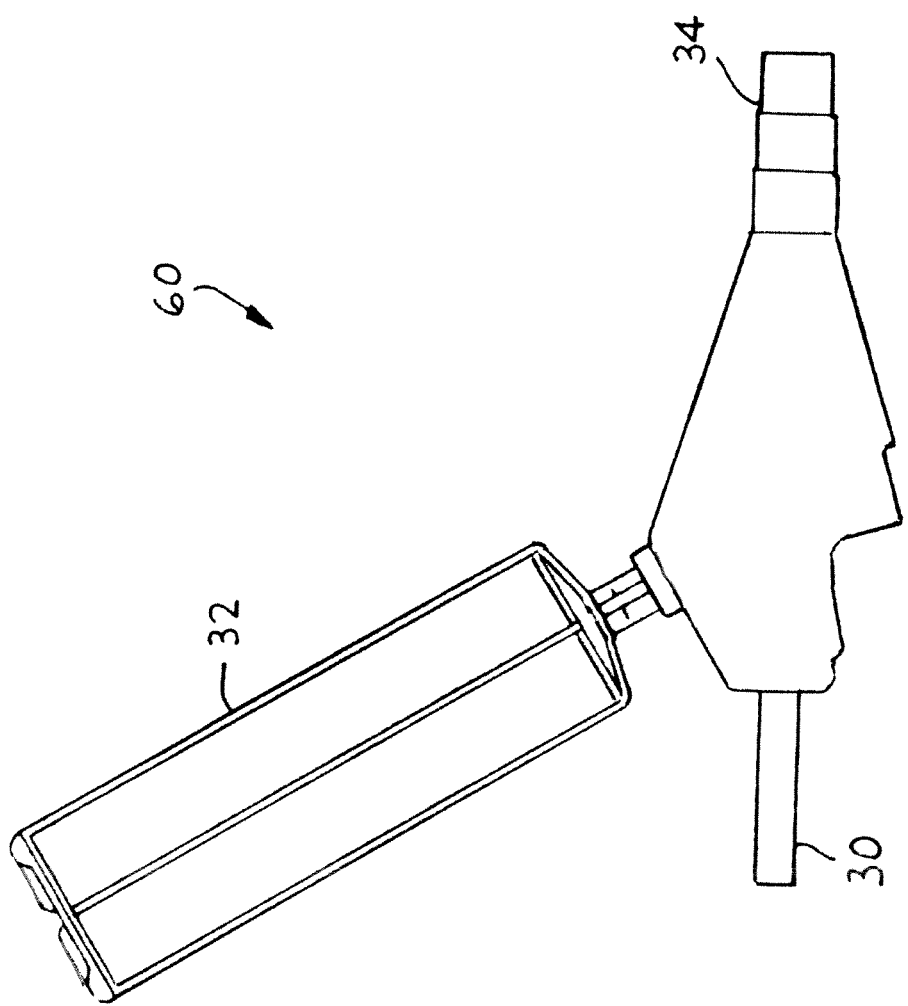

SUBGLOTTIC SUCTIONING SYSTEM

BACKGROUND

Tracheal intubation involves the insertion of a hollow tubular device, known as a tracheal tube, into the trachea of a patient. The tube may be inserted through the mouth or, less desirably, the nose or may be inserted through the neck by way of an incision in the front of the throat. If inserted through the mouth or nose the tube is referred to as an endotracheal tube, if through the front of the throat the tube is referred to as a tracheostomy or trach tube. The two types of tubes will be referred to as tracheal tubes herein. The tracheal tube passes into the trachea and terminates at a position above the carina, anterior to a position between the second and fourth thoracic vertebrate. Gases may then be introduced through the central lumen of the tracheal tube and into the lungs of the patient.

The primary purpose of tracheal intubation is to mechanically ventilate the patient's lungs when the patient is incapable of normal breathing induced ventilation. Intubation may also be used to apply anesthetic gases during surgical intervention. It is desirable to seal the passageway around the tracheal tube in order to maintain enough air pressure to force the air into the lungs during mechanical ventilation and to prevent escape of gases past the tube (i.e. "short circuiting" or bypassing of the lungs). Such a seal may be produced by the use of an inflatable cuff or balloon surrounding the tracheal tube near its distal end. When the tracheal tube has been introduced into the patient's trachea, the inflatable cuff will normally be located about 3 to 5 centimeters above the carina and within the tube-like trachea.

Once inflated, the cuff will engage the wall of the trachea and thereby seal the trachea and prevent the gases being introduced through the tracheal tube from simply reversing course after exiting the distal end of the tube and traveling back up and around the tube to exit the mouth. While treatment of this sort has proved successful for patients having chronic or acute respiratory diseases, there is a constant risk of several complications.

One of the most common complications is known as ventilator associated (or acquired) pneumonia or VAP. Patients receiving tracheal intubation sometimes develop this pneumonia from an infection of the lungs, possibly induced by contaminated pooled secretions entering the trachea and the lungs after bypassing the epiglottis while intubated. The epiglottis normally operates as a valve which selectively closes the entry into the trachea and lungs to prevent the introduction of secretions and particulate matter. However, when a tracheal tube is in place, the epiglottis is held in an open position, and secretions which would normally be directed away from the trachea and into the digestive system instead follow the path of the tracheal tube and pool above the inflatable cuff.

One of the times of greatest risk of such infectious secretions reaching the lungs is upon the cessation of mechanical ventilation. In particular, when the need for tracheal intubation ends, the inflatable cuff of the tracheal tube is deflated so that the tracheal tube may be withdrawn from the patient. The infectious secretions which have pooled in the space above the inflatable cuff are then released and are free to flow into the lungs, where bronchitis or pneumonia may develop. There is also a risk of the infectious secretions reaching the lungs during the time the tracheal tube is in place by aspiration of the secretions that may leak past the tracheal tube cuff.

Removing these secretions from above the tracheal tube cuff would likely reduce the risk of such infections and tracheal tubes having inflatable cuffs and suction means are broadly known in the prior art. It is known, for example, to combine a single lumen suction tube with a tracheal tube. The suction tube provides means for constant suction or evacuation of any pooled secretions which accumulate in the trachea above the inflatable cuff. There remain a number of concerns with such prior art tubes, however. A single lumen for the suction tube under near constant suction often causes direct suction to be exerted on the tracheal mucosa, which may then result in damage to the mucosa. Another major problem with a single suction lumen is that it is also subject to clogging or occlusion, and as a result may be rendered completely useless. Secretions may be quite viscous and can block the opening of the suction lumen above the cuff (the suction port) or can travel into the suction lumen and build up on the inside walls to the point where flow in the lumen is stopped.

A number of attempts have been made to solve some of these problems. U.S. Pat. No. 4,305,392, for example, provides a tracheal tube having a suction lumen that terminates in a suction chamber in the shape of a bulge having four ports in order to avoid damaging the tracheal mucosa. U.S. Pat. No. 4,840,173 provides a suction tube with multiple openings which may be used to evacuate secretions that may pool above the inflatable cuff, again in the hope that the suction line will not adhere to the trachea. U.S. Pat. No. 5,143,062 discloses a double lumen through which air may be circulated, creating an indirect gentle suction through a suction eye communicating with the distal ends of the lumens. This design, however, does not provide adequate suction necessary for aspirating secretions and is easily occluded. US patent publication 2008/0121236 discloses a suction apparatus and connectors that allow a solution to be injected into a suction line. There is no mechanism in the '236 publication to allow the valve to return to a fail-safe or default position where suction is restored to the suction lumen after the user is finished using the apparatus.

The current solution to occlusion of the suction lumen is to remove the tracheal tube and replace it with another one, thus opening the system, or to dispense with suctioning the space above the cuff altogether. Clearly these solutions are unsatisfactory as they negate the purpose for having the suction lumen present. Dispensing with suctioning of secretions from the space above the cuff results in a buildup of such fluids and, when the tube is eventually removed, can allow the fluids present to flow into the lungs, possibly causing VAP. Removing the tube and replacing it involves opening the system and exposes the patient to all of the risks of intubation, low blood oxygen, irritation of the trachea and possible damage to the glottis, etc., as well as the movement of secretions from the space above the cuff to the lungs. Maintaining the patency of the tracheal tube can reduce or delay the risks of extubation, contributing to the likelihood of a successful outcome for the patient.

What is needed is a multilumen tracheal tube or catheter capable of suctioning secretions which have pooled in the space above the inflatable cuff in an effective manner, having a lumen and port that are capable of being cleaned of accumulated secretions without removal of the tube from the patient, so that the system may remain closed. It is also desirable that the system be simple, preferably intuitive, to operate, so that it may be used on a regular basis by nominally trained personnel. The instant disclosure addresses these problems by providing a multilumen tracheal tube and suction lumen system with a rinse function, having a valve that is straight-forward and easy to operate.

SUMMARY

This disclosure relates to a system for a tracheal tube and associated items used for mechanical ventilation. In particular, the present disclosure relates to a tracheal tube having means for irrigating and/or evacuating contaminated secretions accumulating above the tracheal tube cuff and thereby reducing the risk of such contaminated secretions entering the lungs of the patient. The present disclosure improves upon a tracheal tube by incorporating a suction lumen, easily operated valve and ultrathin cuff therein. The suction lumen communicates with the space in the trachea above the cuff where secretions accumulate. Desirably, the tube includes a novel shape for the suction lumen and an enhanced design for the suction lumen port.

The valve is in fluid communication with the suction lumen and with a source of vacuum that may be selectively applied to the suction lumen by a caregiver or user. The valve also has a source of rinsing fluid. The valve may be used to change the suction lumen between communication with the source of vacuum and with the source of rinsing fluid by the caregiver. The alternate supply of rinsing fluid or vacuum to the suction lumen at the discretion of the caregiver allows the suction lumen and the space proximal to the cuff in the trachea to be rinsed and suctioned to loosen and remove secretions that may build up. An excess of secretions has the potential to pass by the cuff into the lower respiratory tract and cause ventilator associated (or acquired) pneumonia (VAP).

Various embodiments of valve designs are provided. All of the valves have the common feature of blocking the source of suction and opening a path for rinsing fluid to the suction lumen when manipulated by the caregiver, and automatically moving back to the source of suction after release. They are designed so that the user may easily and repeatedly alternate suction and rinsing fluid through the suction lumen, i.e., the user may "pulse" the line to loosen, break up and remove secretions and deposits that may partially or completely block or clog the suction lumen, while maintaining a closed system.

In one embodiment, the tracheal tube is formed from a flexible cannula having a length, a distal end, and a proximal end. The cannula consists of a plurality of walls extending substantially along the length of the cannula, dividing the cannula into a plurality of separate lumens including a respiratory lumen, a suction lumen and an inflation lumen. An inflatable cuff surrounds the cannula proximal to the distal end. The inflatable cuff is adapted to seal the trachea of a patient. The inflation lumen is in fluid communication with the inflatable cuff. A port extends through a side wall of the cannula proximal to the inflatable cuff and the port is in fluid communication with the suction lumen.

In other embodiments, the tracheal tube may have a plurality of suction lumens. A rinsing fluid is adapted to be flushed through the suction lumen and extracted via the suction lumen once vacuum is restored.

In still other embodiments, the tracheal tube may be a tracheostomy tube and may have an inflatable cuff having a shape to block a trachea beneath the glottis of the patient. The inflatable cuff surrounds the cannula above the distal end and is adapted, upon inflation, for expansion of the cuff around the distal end portion of the cannula and the proximal end portion of the cannula below a proximal plane of the cannula. The cuff thus seals the trachea below the tracheal stoma and avoids sealing the trachea above the tracheal stoma.

The rinsing fluid may be water, saline, as well as other biocompatible liquids and mucolytic agents. The rinsing fluid may also comprise air or combinations of air and liquids. A medicament, for example, an antiseptic or an antibiotic, or a treatment such as a surfactant may be added to the rinsing fluid to obtain a desired effect on the patient, or to ease suctioning or cleaning of the suction lumen.

DETAILED DESCRIPTION

Reference will now be made to the drawings in which the various elements of the present disclosure will be given numeral designations and in which the disclosure will be discussed so as to enable one skilled in the art to make and use the disclosure. It is to be understood that the following description is only exemplary of the principles of the present disclosure, and should not be viewed as narrowing the pending claims. Those skilled in the art will appreciate that aspects of the various embodiments discussed may be interchanged and modified without departing from the scope and spirit of the disclosure.

Figure 1:
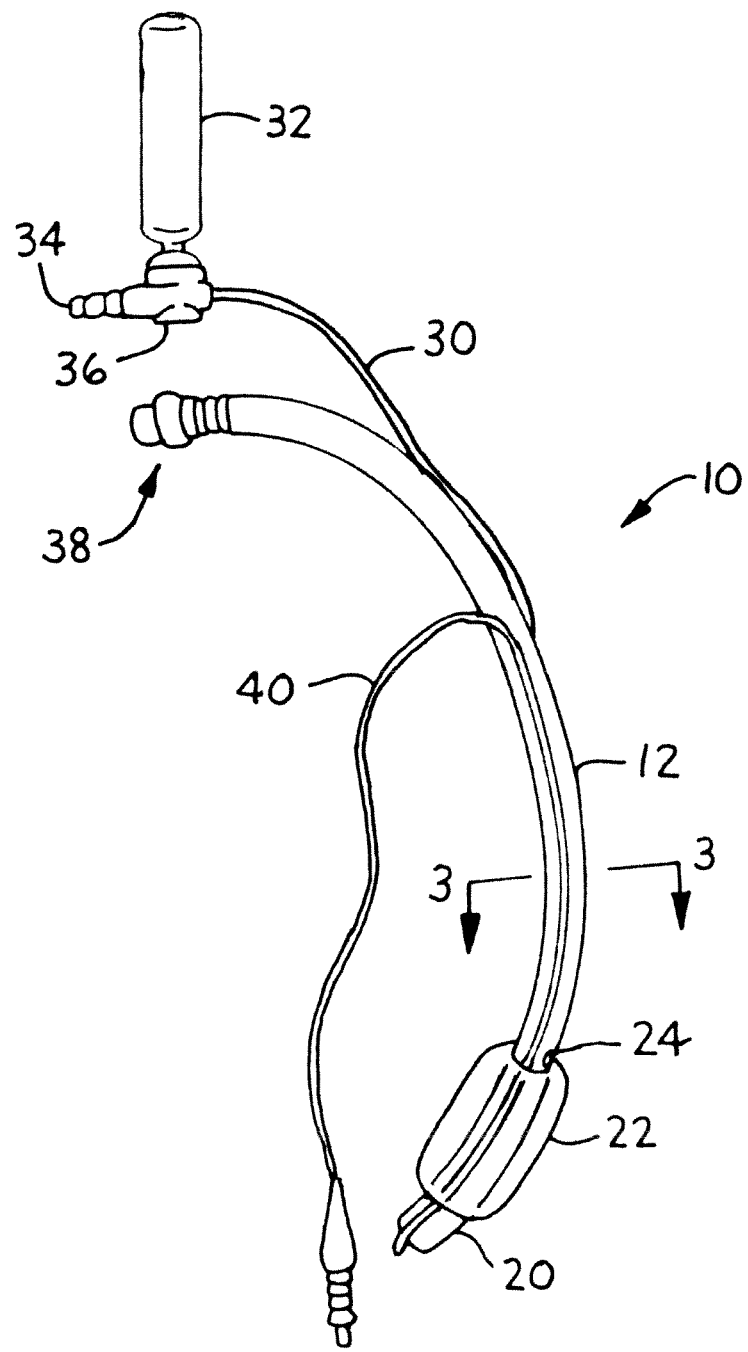
FIG. 1 is a depiction of an endotracheal tube embodiment of a multilumen catheter in accordance with the present disclosure.
Figure 2:
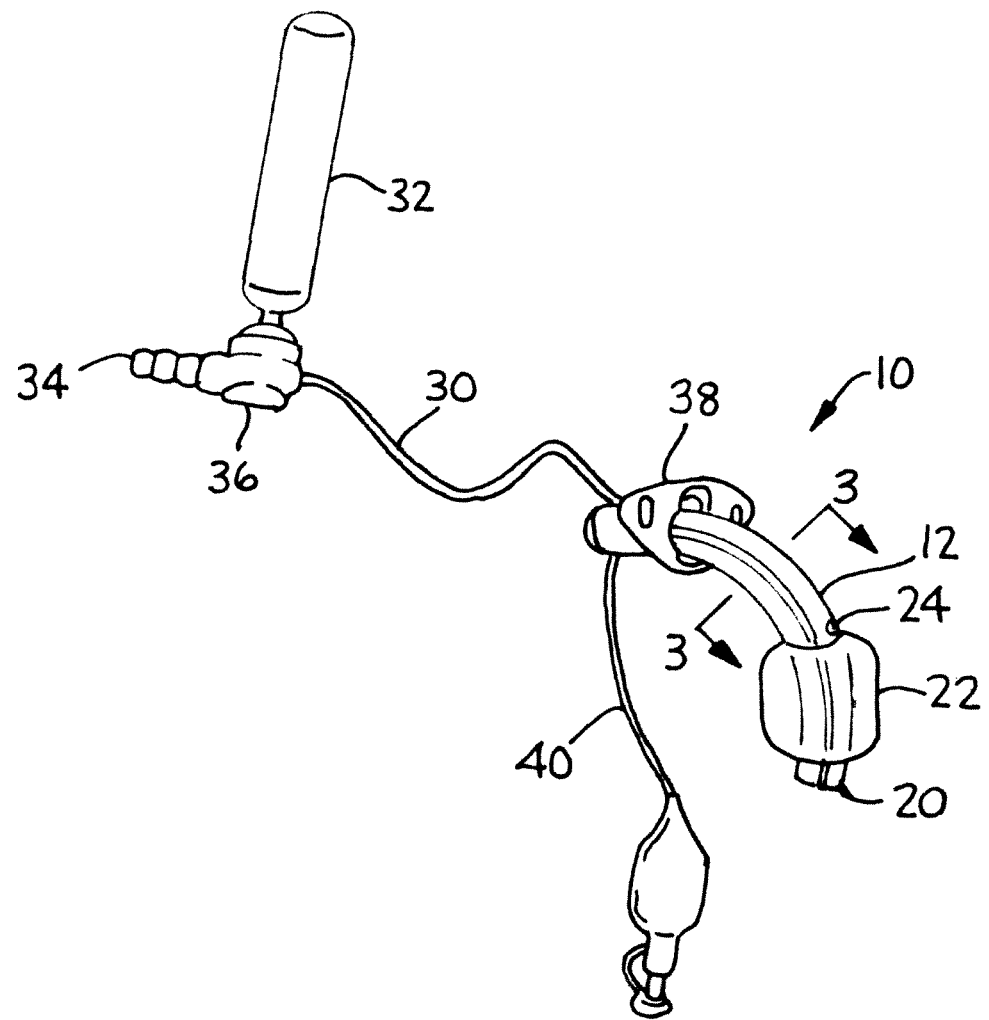
FIG. 2 is a depiction of a trach tube embodiment of a multilumen catheter in accordance with the present disclosure.
Figure 3:
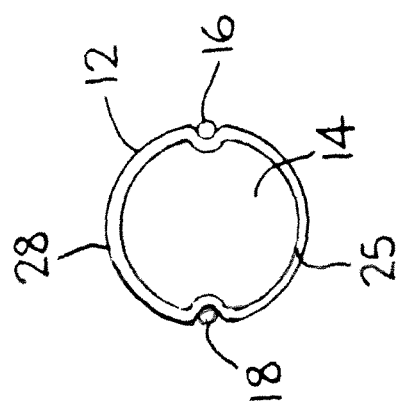
FIG. 3 is a cross-sectional view of the catheter of either FIG. 1 or 2 taken longitudinally through the catheter at 3-3.

Referring to FIGS. 1, 2 and 3, a tracheal tube 10 in accordance with two embodiments of the present disclosure are depicted. FIG. 1 depicts an endotracheal tube, FIG. 2 depicts a tracheostomy (trach) tube and FIG. 3 depicts a cross-section taken at 3-3 in either FIG. 1 or 2.

The tracheal tube 10 in the depicted embodiments is a multilumen cannula 12 having at least one respiratory lumen 14, at least one suction lumen 16, and at least one inflation lumen 18. In these embodiments, each of these lumens is at least partially internal to the cannula 12 (FIG. 3). The respiratory lumen 14 is the largest lumen in the tube, extends through the entire cannula 12 and is adapted to mechanically ventilate a patient (not shown). When the tube 10 is installed in a patient, the distal end 20 of the cannula 12 is situated within the upper respiratory system of the patient.

A balloon, bladder, or inflatable cuff 22 is provided proximal to the distal end 20. An inflation lumen 18 terminates within the cuff 22 on the exterior surface 28 of the cannula 12. The inflation lumen 18 may be within the wall 25 of, or along the surface 28 of the cannula 12 until it is near the proximal end 38 of the tube 10, at which point it becomes a separate tubing line 40 adapted to be used to supply an inflation fluid, generally air, to the cuff 22. The cuff 22 is shaped so that when it is inflated, it blocks the patient's trachea beneath the glottal area. This is known and understood by those skilled in the art to eliminate or at least to minimize the undesirable flow of fluids from the glottal and subglottal regions of the patient into the bronchus and lungs of the patient.

The suction lumen 16 is, similarly to the inflation lumen 18, within the wall 25 or along the external surface 28 of the cannula 12 and terminates at a port 24 on the exterior surface 28 of the cannula 12. The port 24 in the depicted embodiment is near an upper surface of the cuff 22. In this manner, the suction lumen 16 is adapted to suction fluids that collect in the space above the cuff 22 in the patient's trachea (the subglottic area) without negatively impacting ventilation of the patient through the respiratory lumen 14. The suction lumen 16 extends proximally from the suction port 24, along or within the wall 25 of the cannula 12 to a point where it separates from the cannula 12 and becomes a separate tubing line 30. The tubing line 30 is attached to a valve body 36 that is adapted to allow a user to provide suction to the suction lumen 16 from a source of suction (not shown) that is attached to the valve body 36 at a connector 34. The valve body 36 may also be used to provide a rinsing fluid contained within a bullet 32 or other appropriate container, to the suction lumen 16. The functioning of the valve body 36 will be discussed in more detail below.

The rinsing fluid may be introduced into the suction lumen 16 from the bullet 32 while the suction is blocked off by the valve body 36. The rinsing fluid travels down (in a distal direction) the suction lumen 16 as far as is allowed by the condition of the lumen. Desirably the lumen is not completely occluded and allows rinsing fluid to exit at the suction port 24 above the cuff 22 in the trachea. Since the rinsing fluid is usually of a lower viscosity than typical secretions, it has the effect of lowering the viscosity of all of the liquid mix found in the space above the cuff 22 in the trachea once it is introduced. Once the rinsing fluid has been introduced to the suction lumen 16 or the space above the cuff 22 through the suction lumen 16 and the port 24, suction may be restored to the suction lumen 16 and the liquid and any secretions it may have loosened or dissolved may be removed, i.e. sucked out through the suction port 24 and suction lumen 16. This procedure may be repeated as deemed necessary. This procedure is performed at the discretion of the caregiver or user in order to clean secretions and other liquids that may collect and potentially clog the suction lumen 16 or suction port 24. It is important to keep the suction lumen 16 open so that potentially deleterious secretions may be removed from the area above the cuff 22.

The rinsing fluid may comprise water, saline, as well as other biocompatible liquids or mucolytic agents. Mucus may narrow or block the airways, making it difficult to breath. Mucolytic drugs are designed to modify the properties of the mucus to help loosen and clear the mucus from the airways by breaking up the sputum. Common mucolytic agents include erdosteine, acetylcysteine, bromheksin, carbocysteine and guiafenesin. The rinsing fluid may also comprise air or combinations of air and liquids. A medicament, for example, an antiseptic or an antibiotic, or a treatment such as a surfactant may be added to the rinsing fluid to obtain a desired effect on the patient, or to ease suctioning or cleaning of the suction lumen 16.

As can be seen in FIG. 3, the cross sectional view of FIGS. 1 and 2, one possible configuration of the tracheal tube 10 is depicted, more specifically a potential lumen arrangement is depicted within the cannula 12. As can be seen, the suction lumen 16 and the inflation lumen 18 are formed into the wall of the cannula 12. This configuration is of course only meant to suggest one possible arrangement and other arrangements are included in the spirit and scope of the disclosure. The arrangement of lumens within the cannula 12 is not limited in scope to any particular configuration. The layout of the lumens within the cannula 12 may be altered for example or the suction and inflation lumens may be separate lumens not embedded within any one of the walls of the cannula 12.

In other embodiments, a plurality of suction lumens 16 may be provided. Each suction lumen would be configured essentially as described above, in that each would be rinsed by a rinsing fluid provided by a valve 36. A single central valve 36 may be provided to service all suction lumens 16 or a separate, dedicated valve 36 could be provided for each suction lumen 16. Such an arrangement may prove beneficial in more thorough rinsing of the suction lumen or lumens. Alternatively, a plurality of lumens would allow for another lumen to be used should the previous lumen become clogged. Any of these embodiments are easily understood by one of skill in the art as they merely increase the number and arrangement of lumens provided. As such no specific drawings are needed for an understanding of these variations.

As discussed above, the tracheal tube 10 has a cuff 22 around its circumference on a lower (distal) portion of the tube that serves to block the normal air flow in the trachea so that assisted breathing takes place through the tracheal tube using a ventilator. The cuff is desirably made from a soft, pliable polymer such as polyethylene teraphathalate (PETP), low-density polyethylene (LDPE), polyvinyl chloride (PVC), polyurethane (PU) or polyolefin. It should be very thin; on the order of 25 microns or less, e.g. 20 microns, 15 microns, 10 microns or even as low as 5 microns in thickness. The cuff should also desirably be a low pressure cuff operating at about 30 $mmH_2O$ or less, such as 25 $mmH_2O$, 20 $mmH_2O$, 15 $mmH_2O$ or less. Such a cuff is described in U.S. Pat. No. 6,802,317 which describes a cuff for obturating a patient's trachea as hermetically as possible, comprising: a cuff which blocks the trachea below a patient's glottis, an air tube, the cuff being attached to the air tube and being sized to be larger than a tracheal diameter when in a fully inflated state and being made of a soft, flexible foil material that forms at least one draped fold in the cuff when inflated in the patient's trachea, wherein the foil has a wall thickness below or equal to 0.01 mm and the at least one draped fold has a loop found at a dead end of the at least one draped fold, that loop having a small diameter which inhibits a free flow of secretions through the loop of the at least one draped fold. Another description of such a cuff is in U.S. Pat. No. 6,526,977 which describes a dilator for obturating a patient's trachea as hermetically as possible, comprising a cuff which blocks the trachea below a patient's glottis, an air tube, the cuff being attached to the air tube and being sized to be larger than a tracheal diameter when in a fully inflated state and being made of a sufficiently soft, flexible foil material that forms at least one draped fold in the cuff when fully inflated in the patient's trachea, wherein the at least one draped fold formed has a capillary size which arrests free flow of secretions across the cuff by virtue of capillary forces formed within the fold to prevent aspiration of the secretions and subsequent infections related to secretion aspiration. It has been found that the very thin cuff described above is particularly suitable for blocking the flow of lower viscosity fluids that are present above the cuff after the introduction of the rinsing fluid as described herein.

Figure 4:
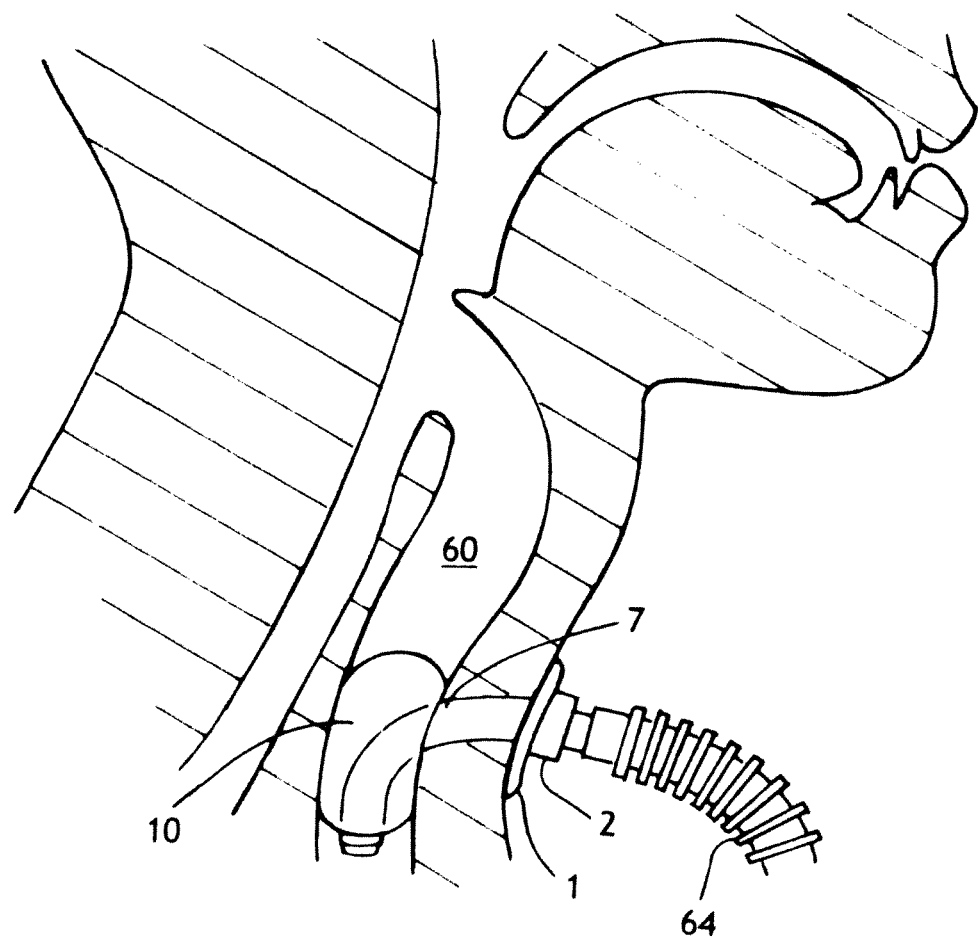
FIG. 4 is a drawing of a cuff for a tracheostomy tube as described in U.S. Pat. No. 6,612,305.
Figure 5:
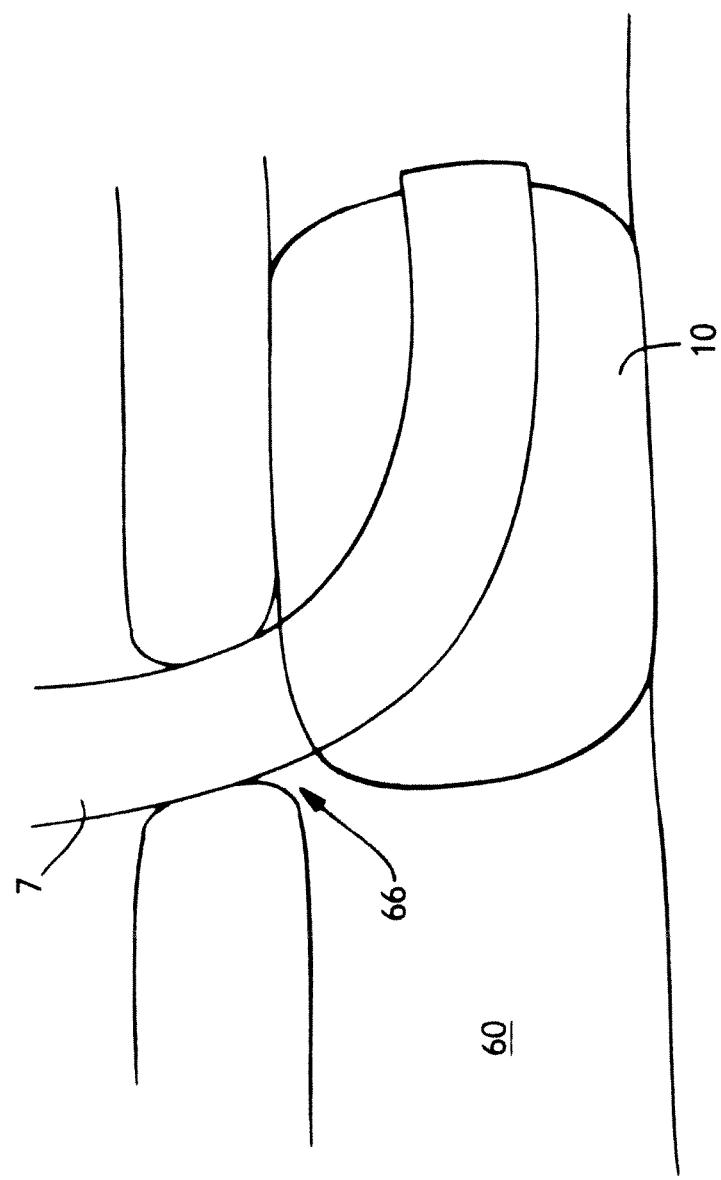
FIG. 5 is a drawing of a cuff for a tracheostomy tube as described in U.S. application 60/994,664.
Figure 6A:
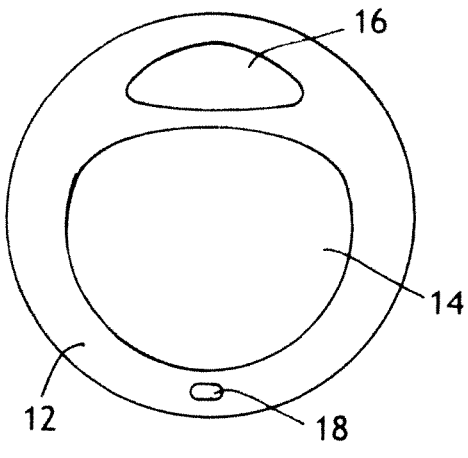
FIG. 6A-H shows various desirable shapes of suction lumens.
Figure 6B:
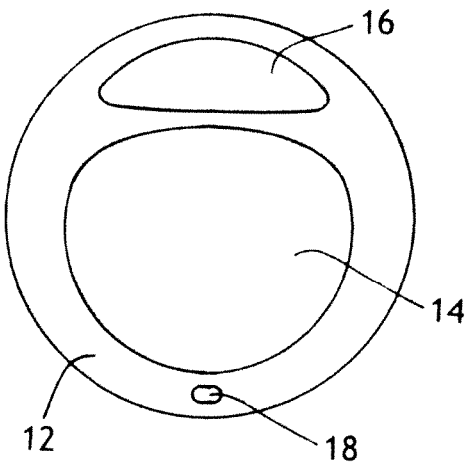
Figure 6C:
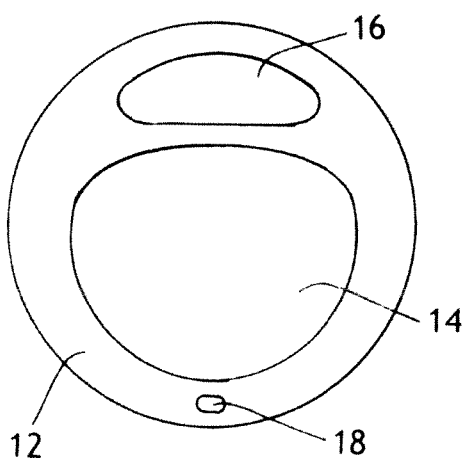
Figure 6D:
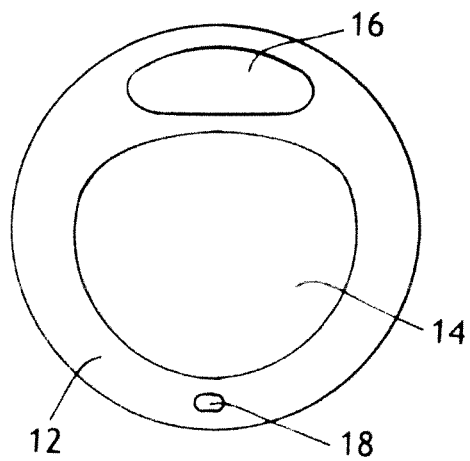
Figure 6E:
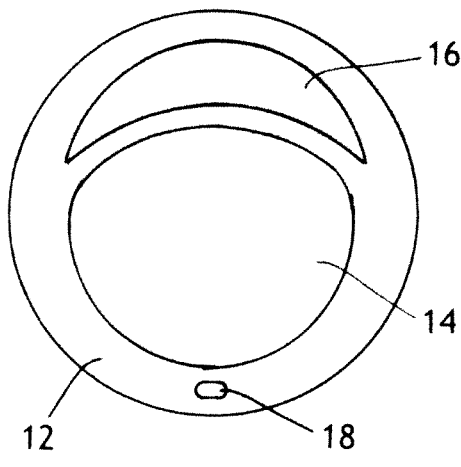
Figure 6F:
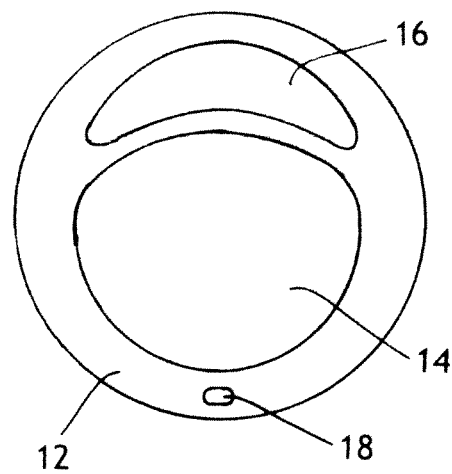
Figure 6G:
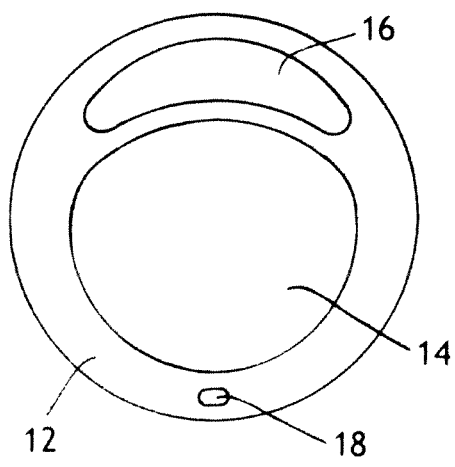
Figure 6H:
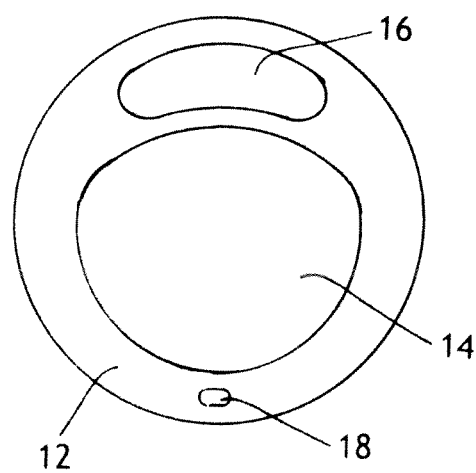

Alternatively, in the particular case of tracheostomy tubes, the cuff may be of a shape as described in U.S. patent application 60/994,664, now Ser. No. 12/206,517 or U.S. Pat. No. 6,612,305. In the '305 patent, the cuff expands not only around the tube, as do the current models, but also cranially to it and to the stoma, sealing the stoma (FIG. 4). This is achieved because the proximal point of attachment and the distal point of attachment of the inflatable cuff on the tube are not contiguous or, in other words, are at an angle ($\alpha$) other than 180 degrees, relative to conventional devices. In the '664 application, the cuff has a distal cuff portion substantially centered about and attached to the distal end portion of the tube. The cuff also has a proximal cuff portion attached to the bend region of the tube and positioned substantially off-center about the bend region below the proximal plane of the device. Upon inflation, this configuration provides for expansion of the cuff around the distal end portion of the tube and the proximal end portion of the tube below the proximal plane of the device to seal the trachea below the tracheal stoma and avoid sealing the trachea above the tracheal stoma (FIG. 5). Desirably, this configuration of the cuff will allow secretions to exit the stoma.

The tracheostomy tube device may have cuff walls that are non-uniform in thickness. For example, the device may have a first portion of the cuff in which the walls have a thickness of about 20 to 30 micrometers and a second portion of the cuff in which the walls have a thickness of about 5 to about 15 micrometers. Desirably, the first portion of the cuff is the portion of the cuff contacting the upper portion of a cross-sectional region of the tracheal lumen and the second portion of the second cuff is the portion of the cuff contacting the lower portion of the same cross-sectional region of the tracheal lumen.

The inflatable cuff component may include a distal end, a distal attachment zone, a proximal end, a proximal attachment zone, an upper region and a lower region, wherein the upper region has a thickness of from about 15 to about 30 micrometers and the lower region has a thickness of from about 5 to about 15 micrometers.

The cuff component may desirably be formed from thermoplastic polyurethane polymers, thermoplastic polyolefin elastomers, thermoplastic polyolefin block copolymers, SBS di-block elastomers, SEBS tri-block elastomers, polyvinyl chloride, polyethylene terephthalate and blends and mixtures thereof.

The suction lumen 16 shown in FIG. 3 may be round, oval or elliptical in shape in currently available commercial tracheal tubes. In an attempt to investigate an improved shape, however, many different configurations were tested. The tests showed that significant differences existed in the flow rate through the lumen, based simply on the shape chosen. It was found that the fluid that accumulated on the proximal side of the cuff was a complicated combination of secretions which were by no means newtonian. The viscosity of the fluid varied substantially, depending on the amount of shear the fluid was subjected to. As various shapes of lumens were investigated, it was found that shear varied within the lumen, with more shear at the bends or corners and less in the center, thus affecting the viscosity and impacting flow. As a result of the investigation, it was found that a more elongated, slightly bent shape performed better than a simple circle, ellipse or oval. A number of such "bent oval", "bean", or "banana" shaped lumens are shown in FIG. 6A-H, which are cross sectional views of a trach tube having a ventilating lumen 14 and a suction lumen 16. More desirably, the bent oval shaped lumens of FIG. 6G, H performed better.

Production of bent oval shaped lumens should prove no more difficult than the production of known round or oval lumens. The tube used to produce tracheal catheters is typically extruded. Changing the extrusion shape is not a difficult matter for those skilled in the art of polymer extrusion.

The suction port opening 24 of FIGS. 1 and 2 has been found to be susceptible to attaching itself to the back of the trachea and causing tissue damage. Continuous suctioning is more of a danger than intermittent suctioning but the potential for suction related tissue damage exists in either method. The suction port 24 is conventionally placed on the cannula 12 in a position where it will be at the lowest point in the trachea above the cuff when the patient is laying on his back, and is conventionally a circular port. This area is where the secretions will naturally accumulate in the greatest amount. This is also an area of the cannula 12 that is subjected to high bending stress and so is more likely to allow the suction port 24 to come into contact with the trachea. One solution to this problem is to move the suction port 24 to a position where it will not come into contact with the trachea should the cannula 12 bend excessively. A position 90 or 180 degrees away from the conventional position depicted in FIGS. 1 and 2 would make tracheal damage less likely, but would also be much less effective in suctioning secretions from the patient lying on his back.

Figure 7:
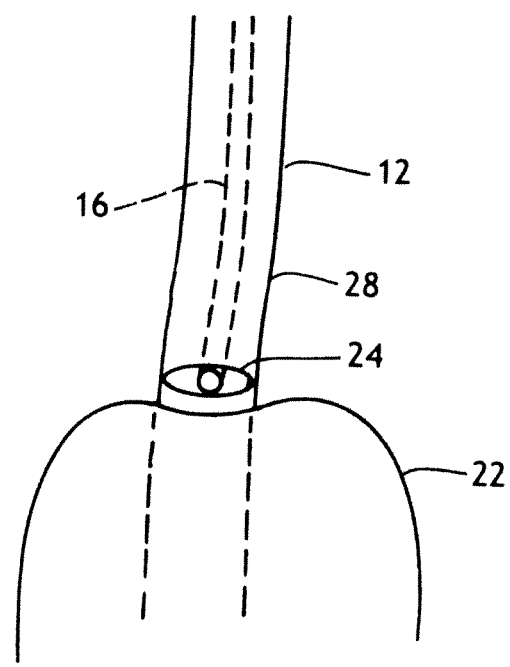
FIG. 7 depicts an elongated suction port on a cannula.

FIG. 7 depicts a suction port 24 on a cannula 12 above the cuff 22 where the suction port 24 is elongated circumferentially around the cannula 12 for some distance. This suction port 24 connects to the suction lumen 16 and also has a shallow extension on either side that reduces the likelihood that the suction port 24 will attach itself to the tracheal wall. The shallow extensions extend a short depth, e.g. a millimeter or two, into the outer surface 28 of the cannula 12 but do not go all the way through the cannula 12 except in the area where the suction port 24 communicates with the suction lumen 16. Should the central part of the elongated suction port 24 come into contact with the trachea, complete suction against the tracheal wall would be avoided because the elongated portions of the suction port 24 would still not be in contact with the tracheal wall. The elongated suction port 24 disclosed herein thus reduces damage to the trachea and helps maintain the suction line open by preventing the cannula 12 from being sucked against the tracheal wall. The elongated suction port 24 may be two to five times wider than the conventional circular port, desirably about three times as wide.

The valve is an important part of the tracheal tube and system of suctioning secretions disclosed herein. The valve is used to suction and rinse the tubing line 30 and by extension the suction lumen 16, suction port 24 and the space in the trachea above the cuff 22. It is desired that the valve have the capability of easily and repeatedly alternately suctioning and providing rinsing fluid through the suction lumen, i.e., the user may "pulse" the line to loosen, break up and remove secretions and deposits that may partially or completely block or clog the suction lumen. It is also desired that the valve automatically (i.e., by itself, without intervention by a user) return to a normal, default or "fail-safe" position in which suction is applied to the system so that secretions are removed, after the user has finished using the valve. If the valve remains in the "rinse" position once the bullet providing rinsing fluid is empty, secretions will build up in the space above the cuff 22 and the purpose for having a suctioning line will be defeated. It is also important that the valve close the access to the suction line prior to opening access to the rinsing fluid bullet, otherwise the fluid will be sucked out of the bullet to the source of suction and wasted. It is also desirable that the valve require a positive action on the part of the user to move it to the rinse position, so that the inadvertent movement of the patient will not activate the valve. Should the patient roll over onto the valve, for example, the valve should remain in the position the caregiver desires, generally the fail-safe or suction position, or should move back to the fail-safe position by itself relatively quickly when the force exerted by the patient is removed. Lastly, it is desired that rinsing and suctioning be capable of being performed and the system kept closed. Removing the bullet, for example, each time suctioning was applied, would repeatedly open the system and allow for the entry of germs. It is true, of course, that the bullet would eventually need to be replaced but this occurs much more rarely than if it needed to be removed each time suctioning were performed. Valves that allow for suctioning and rinsing while the source of rinsing fluid remains in place are desired because maintaining a closed system helps to reduce the chance of infection. The valves described below meet these criteria.

Figure 8:
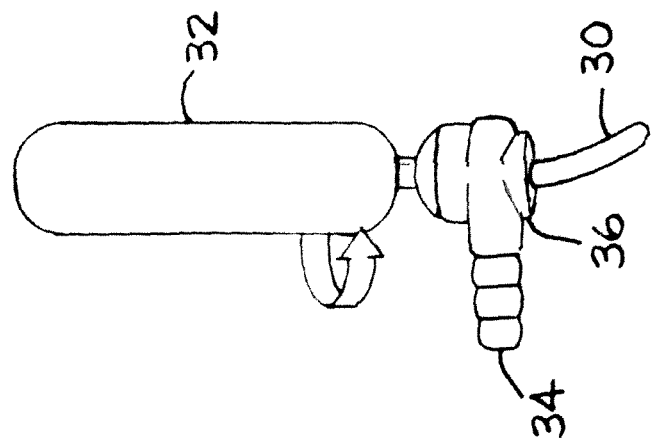
FIG. 8 depicts a rotational rinsing adaptor valve (rotational valve).

In one embodiment, the valve 36 may be as depicted in FIG. 8. This Figure depicts a rotational rinsing adaptor valve (rotational valve) that accommodates a sterile rinsing fluid (e.g. saline) bullet 32 or syringe. The valve 36 may be connected to a vacuum source by a connector 34 and to the suction lumen (not shown) by a tubing line 30. The normal or fail-safe position of the valve is to allow constant suction to the tubing line 30. When rinsing of the suction lumen 16 is desired, a bullet 32 is inserted and is rotated as indicated by the arrow. This rotational movement of the bullet 32 turns a three way valve, blocking the source of suction or vacuum and opening up fluid access from the bullet 32 to the tubing line 30. The tubing line 30 is in fluid communication with the suction lumen 16. The bullet 32 may be squeezed to force the rinsing fluid into the tubing line 30. Once the user has finished instilling rinsing fluid into the lumen, releasing the bullet 32 allows a spring or other automatic means (not shown) to rotate the bullet 32 in the opposite direction, back to its original (normal) position, closing the fluid access from the bullet 32 and re-opening the flow path to the source of vacuum. Re-establishing the fluid communication between the source of vacuum and the tubing line 30 results in suctioning of the suction lumen and the space above the cuff 22 through the suction port 24. The user may repeatedly alternate between suction and rinsing fluid as desired, thus pulsing the system to loosen and remove secretions.

Figure 9:
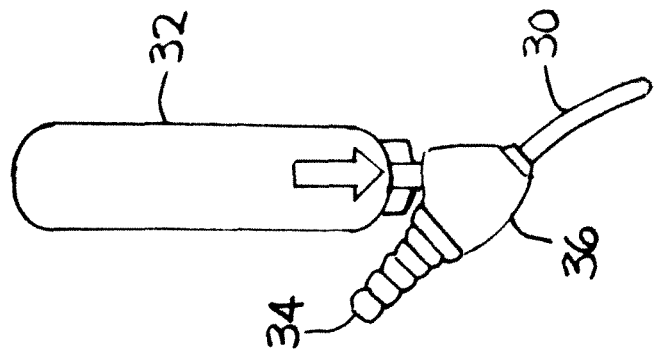
FIG. 9 depicts a push-type rinsing adaptor valve (push valve).

In another embodiment, the valve 36 may be as depicted in FIG. 9. This Figure depicts a push-type rinsing adaptor valve (push valve) that accommodates a sterile rinsing fluid bullet 32 or syringe. The valve 36 may be connected to a vacuum source by a connector 34 and to the suction lumen (not shown) by a tubing line 30. The normal or fail-safe position of the valve is to allow constant suction to the tubing line 30. When rinsing of the suction lumen 16 is desired a bullet 32 containing a rinsing fluid is inserted into the valve 36 as shown. When the bullet 32 is pushed downward toward the valve 36 the bullet 32 blocks the source of vacuum and opens access from the bullet 32 to the tubing line 30 that is in fluid communication with the suction lumen. The bullet 32 may be squeezed to force the rinsing fluid into the tubing line 30. Once the user has finished instilling rinsing fluid into the lumen, releasing the bullet 32 allows a spring or other automatic means (not shown) to move the bullet 32 in the opposite direction, back to its original (normal) position, closing the fluid access from the bullet 32 and re-opening the flow path to the source of vacuum. The user may repeatedly alternate between suction and rinsing fluid as desired, thus pulsing the system to loosen and remove secretions.

Figure 10:
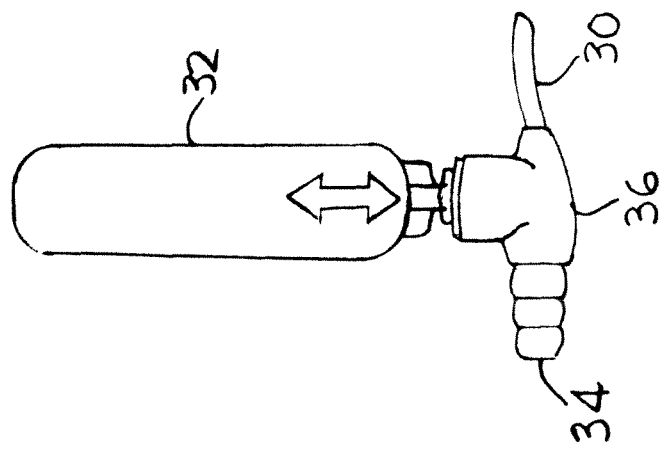
FIG. 10 depicts a straight rinsing adaptor valve (straight valve).

In yet another embodiment, the valve 36 may be as depicted in FIG. 10. This Figure depicts a straight rinsing adaptor valve (straight valve) that accommodates a sterile rinsing fluid bullet 32 or syringe. The valve 36 may be connected to a vacuum source by a connector 34 and to the suction lumen (not shown) by a tubing line 30. The normal or fail-safe position of the valve is to allow constant suction to the tubing line 30. When rinsing of the suction lumen is desired a bullet 32 containing a rinsing fluid is inserted. When the bullet 32 is pushed downward, it blocks the flow path from the suction source to the tubing line 30 and establishes a fluid connection between the bullet 32 and the tubing line 30. The bullet 32 may be squeezed to force the rinsing fluid into the tubing line 30. Once the user has finished instilling rinsing fluid into the lumen, releasing the bullet 32 allows a spring or other automatic means (not shown) to move the bullet 32 in the opposite direction, back to its original (normal) position, closing the fluid access from the bullet 32 and re-opening the flow path to the source of vacuum. The user may repeatedly alternate between suction and rinsing fluid as desired, thus pulsing the system to loosen and remove secretions.

Figure 11A:
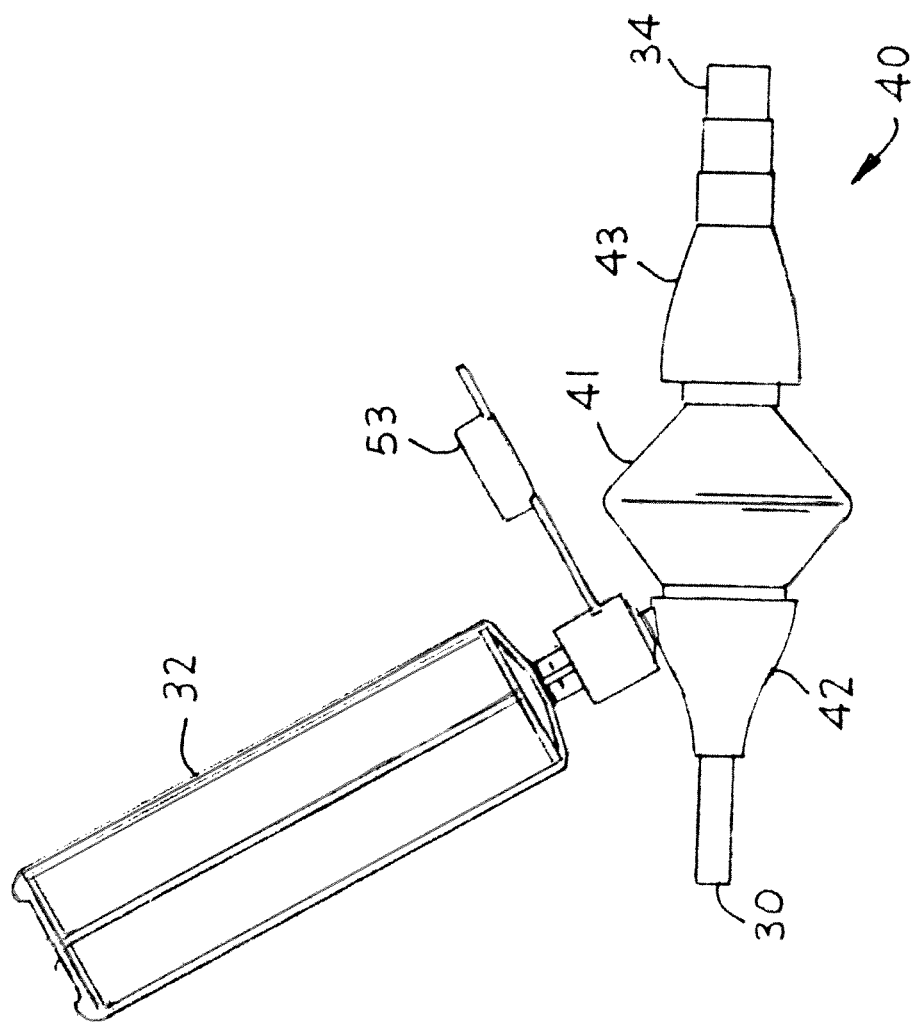
FIGS. 11A and B depict a bellows-type rinsing adaptor valve (bellows valve).
Figure 11B:
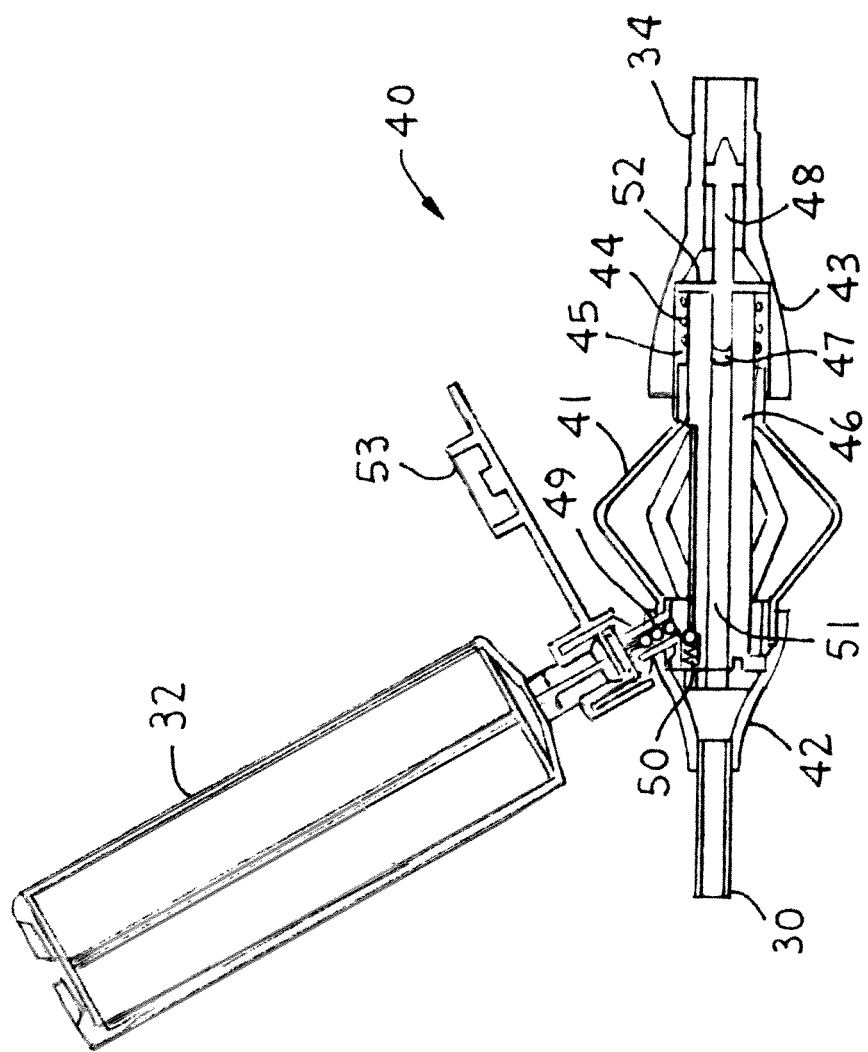

FIGS. 11A and 11B depict a bellows activated suction valve where the cross sectional view is that of FIG. 11B. During suction operation, the connector 34 is connected to a source of suction (not shown). Suctioned fluid or air can travel through the tubing line 30 from the patient end 42, through the center lumen 51 of the piston 46, and then pass through an orifice 47 into the annular space 45 in which is found the spring 44. The suctioned fluid or air may pass around the perpendicular section 52 of the pin 48 and out to the source of suction beyond the connector 34. The pin 48 does not block fluid or air flow but only serves to center and hold in place the other components. Squeezing the bellows 41 flattens the bellows 41 out and forces the spring 44 into the suction end 43. Immediately after the piston 46 begins moving, the piston 46 blocks the flow of fluid or air through the orifice 47. Further squeezing of the bellows opens the rinse (one way) check valve 50, allowing the contents of the bellows 41 to travel into the tubing line 30 toward the patient. Relaxing the squeezing of the bellows 41 allows the spring 44 to force the piston 46 away from the suction end 43 and simultaneously closes the rinse check valve 50. As this occurs and before the orifice 47 is uncovered by the piston 46, the fluid (one-way) check valve 49 opens and rinsing fluid flows from the bullet 32 into the bellows 41. Continued relaxing of the squeezing of the bellows 41 uncovers the orifice 47 and restores suction to the bellows 41. Such a course of action would of course result in the rinsing fluid being sucked out of the bellows 41 toward the source of suction, and would be unproductive. Rather than relax the squeezing of the bellows 41 completely, however, the squeezing of the bellows 41 may be only partially relaxed, allowing rinsing fluid to fill the bellows 41 but not opening the orifice 47. Squeezing of the bellows 41 may be reinitiated, resulting in the closing of the fluid check valve 49 and the rinsing fluid being forced out of the bellows 41, through the rinse check valve 50 and into the tubing line 30 toward the patient. By repeating this squeezing and relaxing of the bellows 41, the caregiver may pulse rinsing fluid into the tubing line 30 and on to the suction port 24 for delivery to the space in the trachea above the cuff 22. This alternating of rinsing fluid and suction may provide a more effective method of removing deposits and secretions than steady state suctioning. The valve 40 may also include a tethered cap 53 that may be used to protect the saline check valve 49 and the rest of the valve 40 from contamination when the bullet 32 is not in place.

Figure 12B:
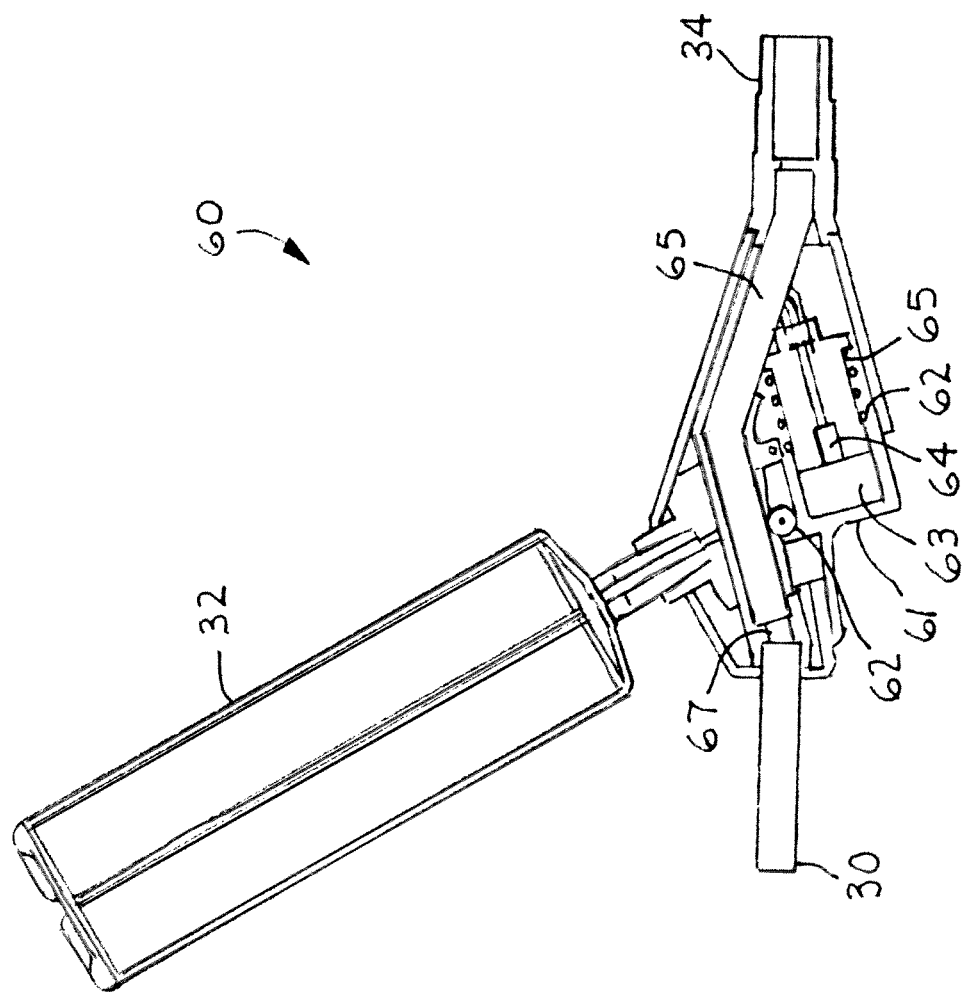
FIGS. 12A and B depict a trigger activated rinsing adaptor valve (trigger valve).

FIGS. 12A and 12B depict a trigger activated suction valve 60 where the cross sectional view is that of FIG. 12B. Squeezing the trigger 61 moves a pivot valve 62 into the closed position, squeezing closed the tubing line 30 within the valve 60 and blocking the source of suction. There are two one-way check valves in the stationary piston 65, a suction lumen check valve and a rinsing fluid check valve. As the trigger continues to move inwards as it is squeezed, it compresses the spring 62, and forces the rinsing fluid in the trigger space 63 through a suction lumen check valve 65, through a narrow tube 66 and into the tubing line 30 at the point 67 where the narrow tube 66 connects to the main tubing line 30. Releasing the trigger 61 allows the spring 62 to push the trigger 61 outward, opening the rinsing fluid check valve and allowing rinsing fluid to flow from the bullet 32, through tubing (not visible) and into the trigger space 63. The pivot valve 62 remains closed until the trigger 61 is entirely released, allowing the user to send repeating pulses of rinsing fluid through the tubing line 30 to the suction port 24. The user may alternatively pulse rinsing fluid into the tubing line 30 and restore suction to the tubing line 30. Upon release of the valve, the spring automatically opens access from the source of suction to the suction lumen and closes access from the bullet to the suction lumen. One skilled in the art may readily see that the trigger may be positioned on an upper surface of the valve 60 or on a side, as desired, and still be within the teachings and inventive spirit of the active trigger valve presented herein.

Figure 13A:
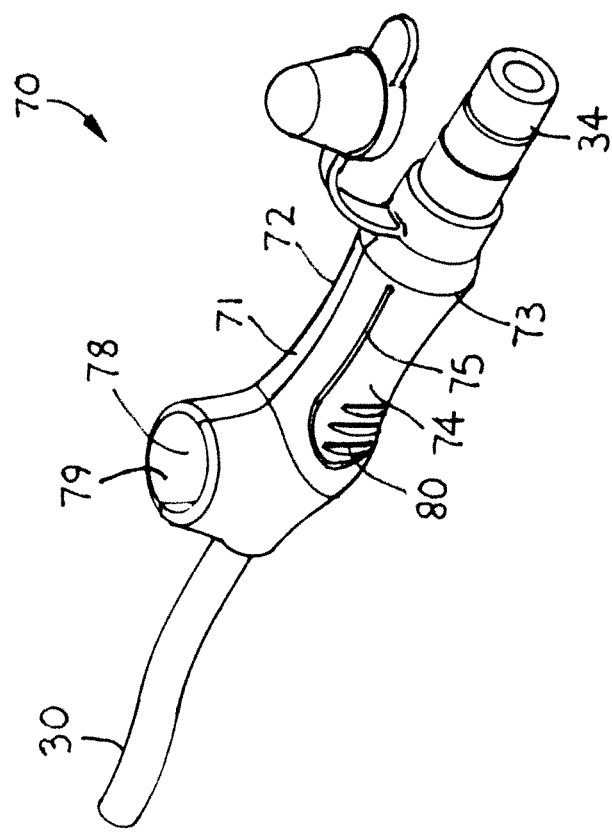
FIGS. 13A and B depict an in-line pinching rinsing adaptor valve (pinch valve).

FIG. 13A and its exploded view 13B depict an in-line pinching rinse valve 70. This relatively less complicated valve has a body 71 that, in this embodiment, is made from two mirror image halves; a right half 72 and a left half 73 where the forward portion of the valve is defined as the patient facing end that connects to the tubing line 30. Note that the body may alternatively be made from a top and bottom half or may be made as a single piece. The rear portion of the valve 70 is a connector 34 for the source of suction (not shown). At least one of the body halves has a peninsular tab 74 (only visible on the left half 73 in the Figures) that is separated from its body half by a slight gap 75 for much of its length. The peninsular tab 74 remains attached to its body half at one end. The gap 75 allows the peninsular tab 74 to flex and move relative to the body half without breaking, provided the material from which the body half is made is sufficiently thin and or flexible, and to spring back to its original position upon release of the squeezing force. On the interior of at least one body half should be a ridge 76, desirably placed perpendicularly to the crimp tubing 77, that is sized so that when the peninsular tab 74 is squeezed by a user's fingers, the ridge 76 will contact an internal length of crimp tubing 77 and, if sufficient force is applied, close the lumen of the crimp tubing 77 and block the communication of the source of suction through the crimp tubing 77. The exact size and shape of the peninsular tab 74 and the ridge 76 may be varied according to the desire of the valve designer and remain within the teachings of this disclosure, provided the lumen of the crimp tubing 77 may be closed by squeezing the peninsular tab(s) 74. For example, the ridge 76 may, instead of being a rectangular feature as shown in the Figure, be another shape like a round or oval bump that is placed in a position to come into contact with the crimp tubing 77 when the peninsular tab(s) 74 are squeezed together. It is also possible to design the peninsular tab(s) 74 in a way such that the ridge 76 is deleted entirely from the body halves and the peninsular tab(s) 74 directly impinge upon the crimp tubing 77 and close its lumen.

The patient facing end of the crimp tubing 77 is in fluid communication with the tubing line 30 that in turn communicates with the suction lumen 16 and suction port 24, discussed previously. The other end of the crimp tubing 77 is in fluid communication with the connector 34 that further communicates with the source of suction. The valve 70 has an inlet 78 to receive rinsing fluid from a bullet. The valve 70 desirably has an adapter 79 that is designed to accept the bullet and fit snugly against it to reduce fluid leakage, and a check valve 80 through which the saline solution will flow from the bullet. The check valve 80 requires more force to open it than is exerted by the source of suction alone, thus requiring the user to squeeze the bullet to provide sufficient force to open the check valve 80 and move rinsing fluid into the tubing line 30. An optional tethered cap (not shown) adapted to cover the inlet 78 when a bullet is not in place may be provided.

When fully installed and in use, a user may simply squeeze the peninsular tab(s) 74 on the body 71 with one hand to close the lumen of the crimp tubing 77 and block the source of suction from the tubing line 30, and, keeping the crimp tubing 77 closed, squeeze the fluid bullet with the other hand to force liquid into the tubing line 30 and on toward the space above the cuff 22 in the trachea. It has been found that users generally prefer to perform one function with each hand, and that requiring more than one function to be performed with one hand can cause confusion. It is advantageous, therefore, that this valve has one function for each hand. Once the desired amount of fluid is dispensed, the user may stop squeezing the bullet and relax pressure on the peninsular tab(s) 74. This permits the peninsular tab(s) 74 to spring back to the original position, allowing the crimp tubing 77 to resume its normal shape and restoring suction to the tubing line 30. The user may repeatedly alternate between suction and rinsing fluid as desired, thus pulsing the system to loosen and remove secretions, without removing the bullet.

In embodiments where the body 71 of FIG. 13A is made of a single piece, the tubing line 30 may be slid into the interior of the body 71 and mated with the connector 34, thus dispensing with a separate piece acting as the crimp tubing 77. In this case, the tubing line 30 may be punctured for access by the source of rinsing fluid.

Should gloves become caught in the gap 75, the body 71 may be wrapped with a polymeric material like a "shrink wrap" plastic that shrinks in place in response to heat, for example, to cover over the gap 75 and prevent glove entrapment in the gap 75. Further, the peninsular tab(s) 74 may have surface topography 80 like lines, chevrons, dimples, reverse dimples and the like, in order to improve the tactile sensation felt by a user wearing gloves and to improve the quality of the user's grip on the body 71.

In a particular embodiment, the valve 70 of FIG. 13A may have body halves that are between 3 and 10 cm in length, desirably about 7 cm in length and between 0.5 and 2 cm in diameter, desirably about 1.7 cm. Two peninsular tabs 74 located opposite each other may be between 1 and 5 cm in length, desirably about 2.5 cm and a ridge 76 may be located approximately in the lengthwise center of each peninsular tab 74. The gap 75 may be between 0.3 and 3 mm in width, desirably about 1 mm.

Figure 13B:
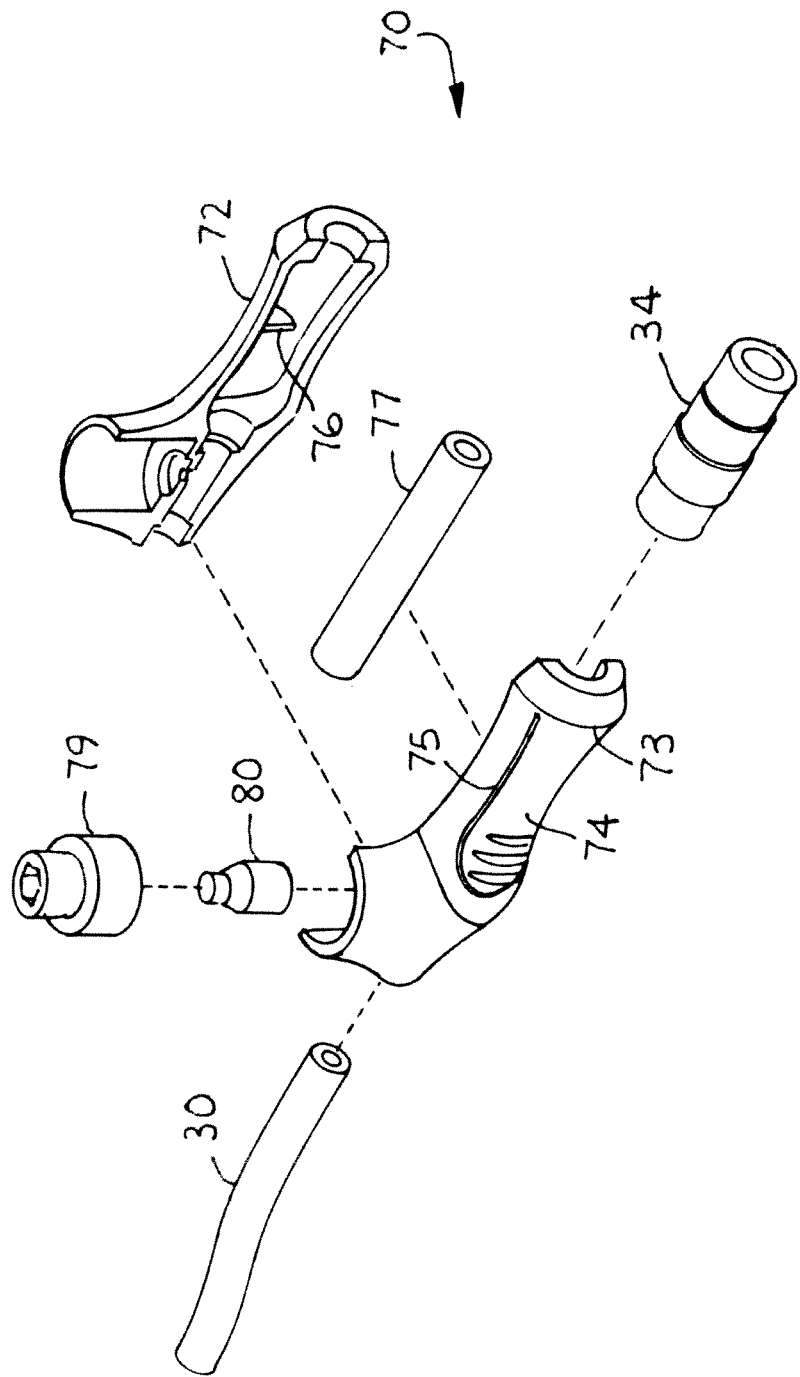
Figure 14:
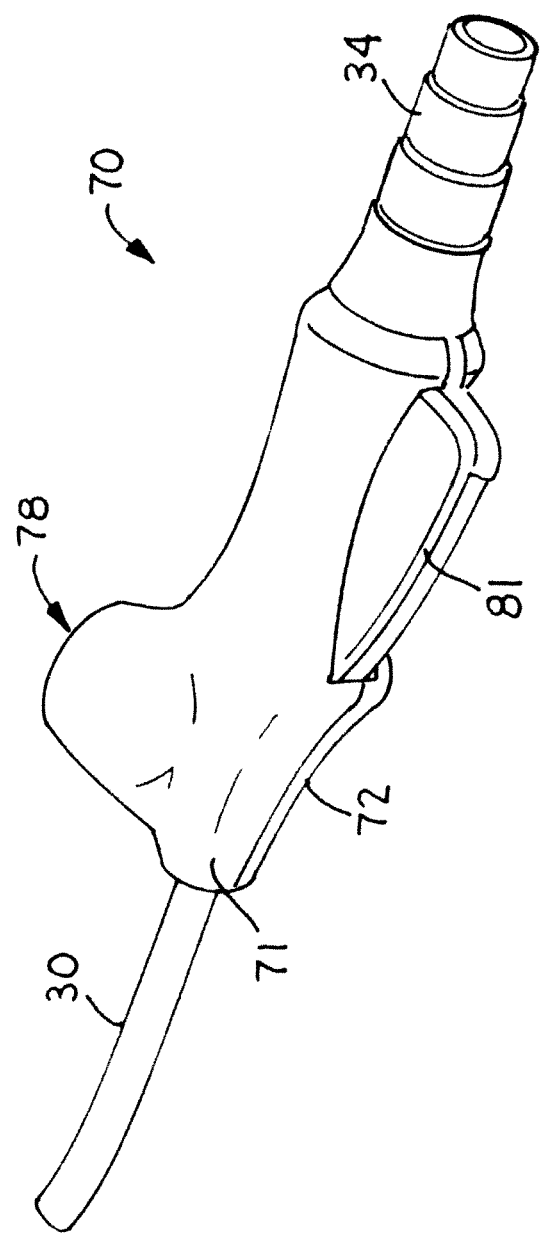
FIG. 14 depicts an in-line valve having a trigger tab that blocks flow.

FIG. 14 shows another embodiment that, like the valve of FIG. 13, allows for one handed operation of the valve. This valve 70 is similar in many ways to the valve of FIG. 13 but differs in the method of activation. In the valve 70 of FIG. 14, depressing a trigger tab 81 on the bottom of the valve 70 results in crimping the tubing inside the body and closing it. Releasing the trigger tab 81 allows the crimp tubing (not shown) to re-open and re-establishes communication between the source of suction and the suction lumen.

Figure 15:
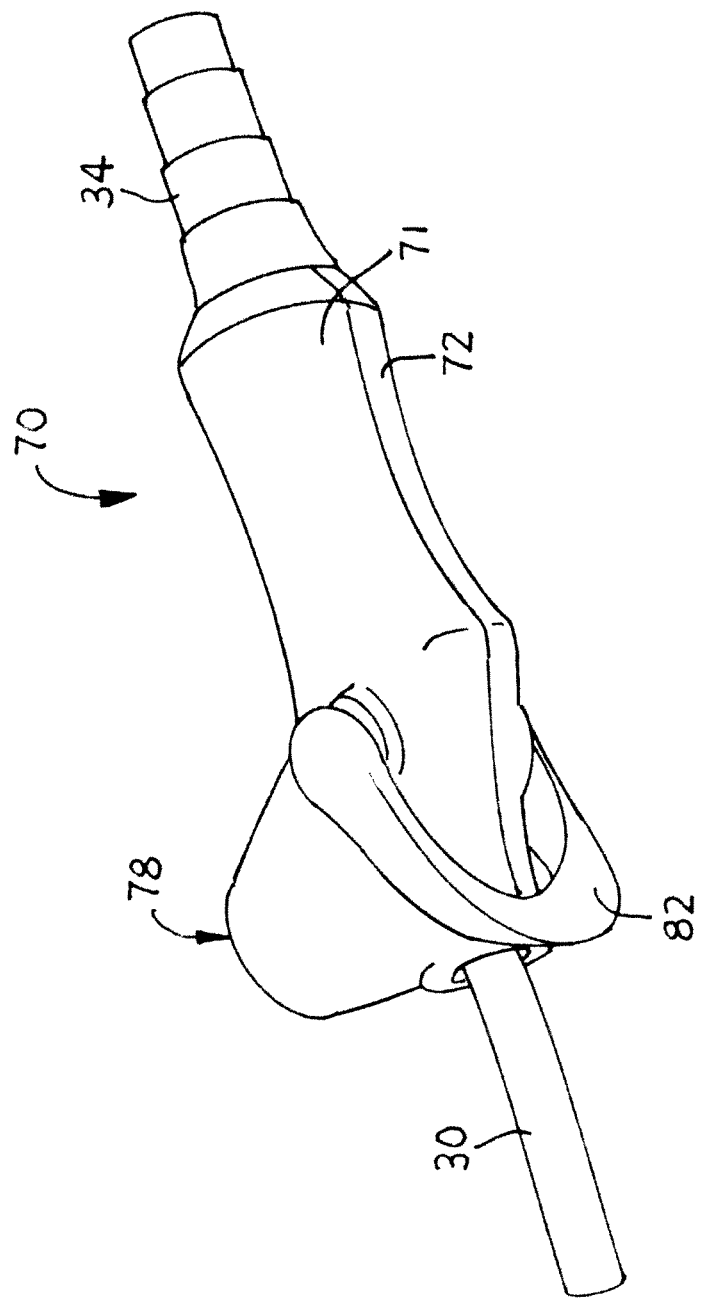
FIG. 15 depicts an in-line valve having a trigger bar that blocks flow.

FIG. 15 shows another embodiment that, like the valve of FIG. 13, allows for one handed operation of the valve. This valve 70 is similar in many ways to the valve of FIG. 13 but differs in the method of activation. In the valve 70 of FIG. 14, moving a trigger bar 82 on the bottom of the valve 70 rearward (toward the connector 34 for the source of suction) results in crimping the tubing inside the body and closing it. Releasing the trigger bar 82 allows the crimp tubing (not shown) to re-open and re-establishes communication between the source of suction and the suction lumen.

The materials of construction of the valves disclosed herein may be, for the bodies, polyolefins like polyethylene and polypropylene, nylons, polycarbonates, acrylonitrile butadiene styrene (ABS), acrylics, PVC and the like. Particularly suitable is high density polyethylene (HDPE). Materials of construction of the flexible parts like the check valves and tubing include silicones, polyurethanes, polyethylene terephthalate (PET), low-density polyethylene (LDPE), polyvinyl chloride (PVC), or elastomeric-based polyolefins.

In use, a medical care provider would insert the tracheal tube 10 into the patient's trachea in a manner known and understood by those of skill in the art; through oral or nasal intubation or through a tracheostomy. The inflatable cuff 22 would be inflated by air supplied through the inflation lumen 18 so as to sealingly engage the walls of the patient's trachea. This would effectively prevent or at least minimize flow of undesirable fluids from the subglottic space into the bronchus and lungs. Ventilation of the patient through the respiratory lumen 14 may occur at this time and continue for as long as necessary.

At the discretion of the caregiver, the subglottic space within the patient's trachea may be suctioned through the suction lumen 16 via the port 24 through the wall 25 of the cannula 12. Such suctioning may be performed continuously or intermittently as desired. Also at the discretion of the caregiver, the suction lumen 16 and/or the space above the cuff 22 may be rinsed and suctioned. This is accomplished by blocking the source of suction from the suction lumen 16 through the use of the valve 36 and introducing a rinsing fluid from a bullet 32 to the suction lumen 16 as described in more detail above. After the liquid has been introduced, the valve 36 is re-opened to the source of vacuum and suction restored, thus evacuating the suction lumen 16 and removing any secretions and other liquids in the suction lumen 16 and, desirably, any secretions accumulated above the cuff 22. A treatment may be added to the rinsing fluid such as a medicament, for example, an antiseptic, antibiotic or mucolytic agent. In that case, it may be desirable to allow more time between the introduction of the rinsing fluid and the evacuation of the rinsing fluid from the lumen and cuff area so as to gain the desired therapeutic effect prior to suctioning.

While the invention has been described in detail with respect to specific embodiments thereof, it will be apparent to those skilled in the art that various alterations, modifications and other changes may be made without departing from the spirit and scope of the invention. It is therefore intended that the claims cover all such modifications, alterations and other changes encompassed by the appended claims.

We claim:

1. A subglottic suctioning system comprising a tracheal tube having:
    a flexible cannula having a length, a distal end, and a proximal end, the cannula comprising a plurality of separate lumens including a respiratory lumen, a suction lumen and an inflation lumen;
    an inflatable cuff surrounding the cannula above the distal end and adapted to seal the trachea of a patient and further having the inflation lumen in fluid communication with the inflatable cuff; and
    a port extending through a side wall of the cannula proximal to the inflatable cuff, the port in fluid communication with the suction lumen; and
    a valve body located proximal to the cannula, the valve body having
        an in-line pinch valve on the suction lumen on a proximal end of the body that allows a user to pinch the suction lumen closed with a first hand, and
        a check valve that operates independently of the in-line pinch valve and through which rinsing fluid will flow from a bullet or syringe into the suction lumen distal to the pinch valve when the bullet or syringe is squeezed by a user with a second hand,
        wherein the in-line pinch valve returns to an open position when the user stops pinching the valve and the check valve closes and stops the flow of rinsing fluid when the user stops squeezing the bullet or syringe.

2. The tracheal tube of claim 1, wherein the port is elongated circumferentially around the cannula.

3. A tracheostomy tube comprising:
    a flexible cannula having a length, a distal end, and a proximal end, the cannula comprising a respiratory lumen, a suction lumen and an inflation lumen;
    an inflatable cuff surrounding the cannula above the distal end and adapted upon inflation, for expansion of the cuff around the distal end portion of the cannula and the proximal end portion of the cannula below a proximal plane of the cannula to seal the trachea below the tracheal stoma and avoid sealing the trachea above the tracheal stoma and further having the inflation lumen in fluid communication with the inflatable cuff; and
    a port extending through a side wall of the cannula proximal to the inflatable cuff, the port in fluid communication with the suction lumen; and
    a valve body between the cannula and a source of suction having a means for blocking the suction lumen adapted to allow a user to pinch the suction lumen with a first hand, the valve body further having a source of rinsing fluid that passes through a check valve that operates independently of the means for blocking the suction lumen and that adapted to be applied to the suction lumen at the discretion of a caregiver with a second hand by manipulation of the source of rinsing fluid, and wherein vacuum is automatically re-applied upon release of said means for blocking the suction lumen.

4. The tracheal tube of claim 3, wherein the port is elongated circumferentially around the cannula.

* * * * *